(12) United States Patent
Hudson et al.

(10) Patent No.: US 10,258,941 B2
(45) Date of Patent: Apr. 16, 2019

(54) APPARATUS AND METHODS FOR PREPARING AN EMULSION

(75) Inventors: Bruce W. Hudson, Pleasant Grove, AL (US); Gary W. Opperman, St. Louis Park, MN (US); Adrian T. Raiche, Helena, AL (US)

(73) Assignee: Evonik Corporation, Parsippany, NJ (US)

( * ) Notice: Subject to any disclaimer, the term of this patent is extended or adjusted under 35 U.S.C. 154(b) by 372 days.

(21) Appl. No.: 13/334,154

(22) Filed: Dec. 22, 2011

(65) Prior Publication Data

US 2012/0178629 A1 Jul. 12, 2012

Related U.S. Application Data

(60) Provisional application No. 61/426,705, filed on Dec. 23, 2010.

(51) Int. Cl.
*A01N 25/04* (2006.01)
*B01F 3/08* (2006.01)
*B01F 5/06* (2006.01)
*B01J 19/00* (2006.01)

(52) U.S. Cl.
CPC .......... *B01F 3/0807* (2013.01); *B01F 5/0696* (2013.01); *B01J 19/006* (2013.01); *B01J 2219/00768* (2013.01); *B01J 2219/00772* (2013.01); *B01J 2219/30207* (2013.01); *B01J 2219/30296* (2013.01); *B01J 2219/30408* (2013.01); *B01J 2219/30416* (2013.01); *B01J 2219/312* (2013.01)

(58) Field of Classification Search
None
See application file for complete search history.

(56) References Cited

U.S. PATENT DOCUMENTS

| | | | |
|---|---|---|---|
| 3,682,446 A | 8/1972 | Eron | |
| 4,061,313 A | 12/1977 | Brauner et al. | |
| 4,259,186 A | 3/1981 | Boeing et al. | |
| 6,706,289 B2 | 3/2004 | Lewis et al. | |
| 7,268,167 B2 | 9/2007 | Higuchi et al. | |
| 7,776,927 B2 | 8/2010 | Chu et al. | |
| 8,916,196 B2 | 12/2014 | Zeigerson | |
| 2005/0032238 A1 | 2/2005 | Karp et al. | |
| 2006/0108012 A1 | 5/2006 | Barrow et al. | |
| 2007/0190154 A1* | 8/2007 | Zeigerson | 424/489 |
| 2007/0207211 A1 | 9/2007 | Zeigerson | |
| 2007/0214831 A1 | 9/2007 | Nanda | |

FOREIGN PATENT DOCUMENTS

| | | |
|---|---|---|
| DE | 4336983 A1 | 5/1995 |
| EP | 0077652 A1 | 4/1983 |
| EP | 2002882 A1 | 12/2008 |
| JP | 54-153468 | 10/1979 |
| JP | 57201519 A | 12/1982 |
| JP | 04-193337 A | 7/1992 |
| JP | 2003-513905 A | 4/2003 |
| WO | WO-2012/088409 A2 | 6/2012 |

OTHER PUBLICATIONS

International Search Report and Written Opinion dated Jul. 9, 2012 for Intl. App. No. Intl. App. No. PCT/US2011/066833, filed on Dec. 22, 2011 (Inventor—Hudson et al.; Applicant—Evonik Degussa Corp.; pp. 1-25).

* cited by examiner

*Primary Examiner* — David Browe
(74) *Attorney, Agent, or Firm* — Linda S. Li; Jason S. Ngui; Bernard Lau (57) ABSTRACT

Disclosed herein are apparatus and methods for producing emulsions, and, in particular, for maintaining laminar flow during production of emulsions containing microsuspensions. Disclosed herein are columns for receiving a packing material that permits fluid flow through the column. The columns have a periphery that defines an interior cavity in fluid communication with inlets and outlets of the column. Disclosed herein is a method of preparing an emulsion that includes (1) forming a first phase typically containing an organic solvent, a polymer, and one or more biologically active agents and/or chemicals; (2) forming a second phase typically containing water as the second solvent, an emulsion stabilizer and optionally a solvent; and (3) passing the first and the second phases through the column to form a "water in oil" type emulsion.

10 Claims, 7 Drawing Sheets

APPARATUS AND METHODS FOR PREPARING AN EMULSION

CROSS-REFERENCE TO RELATED APPLICATIONS

This patent application claims priority to U.S. Provisional Patent Application Ser. No. 61/426,705, entitled "APPARATUS AND METHODS FOR PREPARING AN EMULSION" and filed on Dec. 23, 2010, the entirety of which is incorporated herein by reference.

FIELD

The invention relates to an apparatus for preparing an emulsion, a method of using such apparatus, and a composition made by the method of the invention. More particularly, the disclosed apparatus is a column having dividers for partitioning a packing material and directing fluid flow through the column to produce an emulsion product.

BACKGROUND

Encapsulation of pharmaceuticals in biocompatible, biodegradable polymer microparticles can prolong the maintenance of therapeutic drug levels relative to administration of the drug itself. Sustained release may be extended up to several months depending on the formulation and the active molecule encapsulated. In order to prolong the existence at the target site, the drug may be formulated within a matrix into a slow release formulation. Following administration, the drug then is released via diffusion out of, or via erosion of, the matrix. Encapsulation within biocompatible, biodegradable polyesters, such as, for example, copolymers of lactide and glycolide, has been utilized to deliver small molecule therapeutics ranging from insoluble steroids to small peptides. Presently, there are over a dozen lactide/glycolide polymer formulations in the marketplace, the majority of which are in the form of microparticles.

In addition, U.S. Pat. No. 6,706,289, hereby incorporated in its entirety by reference, discloses controlled release formulations of biologically active molecules that are coupled to hydrophilic polymers such as polyethylene glycol and methods of their production. The formulations are based on solid microparticles formed of the combination of biodegradable polymers such as poly(lactic acid) (PLA), poly(glycolic acid) (PGA), and copolymers thereof.

Several techniques for the production of microparticles containing biological or chemical agents by an emulsion-based manufacturing technique have been reported. In general, the methods have a first phase consisting of an organic solvent, a polymer and a biological or chemical agent dissolved or dispersed in the first solvent. The second phase comprises water and a stabilizer and, optionally, the first solvent. The first and the second phases are emulsified and, after an emulsion is formed, the first solvent is removed from the emulsion, producing hardened microparticles.

In one technique, two immiscible solutions are added to a packed bed of spherical beads within an emulsion column. Ideally, the two solutions have a combined mass flow rate that creates laminar flow conditions. The flow of the solutions is repeatedly divided and recombined to create homogenous fluid volumes that contain a portion of each immiscible solution. The lesser portion separates into spherical droplets as a dispersed phase in the larger portion (the continuous phase). The repeated division and recombination is critical to the formation of the homogenate.

As the above technique is adjusted to a larger scale, there is a parametric increase in the potential path length that must be traveled by each fluid element. These increases in path length lead to increases in the residence time of the fluid elements in the packed bed emulsion column. The increases in residence time, in turn, can impact the physical properties of the final emulsion product.

Another problem that arises during scale up of a packed bed emulsion column is the formation of preferred channels for fluid travel within the packed bed. The formation of preferred channels leads to "virtual columns," through which flow is increased relative to a mean flow rate, and "static areas," where flow is decreased relative to the mean flow rate. The presence of these "virtual columns" and "static areas" impacts the number of homogenization events and other parameters of emulsion formation.

Thus, easily scalable apparatus and methods are needed for forming emulsion-based microparticles that provide a narrow, reproducible, particle size distribution, capable of use with both large and small volumes. More particularly, there is a need in the pertinent art for a column that is configured to maintain a consistent path length and to prevent formation of preferred channels in a packed bed during scale-up of an emulsion process.

SUMMARY

Disclosed herein are columns for receiving a packing material that permits fluid flow through the column. The columns have a periphery that defines an interior cavity in fluid communication with inlets and outlets of the column. In one aspect, the inlet of the column receives at least one fluid. In another aspect, the column includes at least one divider positioned within the interior cavity. In an additional aspect, each divider extends along at least a portion of the longitudinal length of the interior cavity of the column. In a further aspect, the dividers are configured to partition the packing material and to direct fluid flow through the column. Methods of preparing emulsions using the disclosed columns are also described.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

The present invention can be understood more readily by reference to the following detailed description, examples, and claims, and their previous and following description. However, before the present compositions, articles, devices, and/or methods are disclosed and described, it is to be understood that this invention is not limited to the specific compositions, articles, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its currently known embodiments. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Before the present microparticles, copolymers, polymer admixtures, compounds, compositions, and/or methods are disclosed and described, it is to be understood that the aspects described herein are not limited to specific compounds, synthetic methods, or uses as such can, of course, vary. It is also to be understood that the terminology used herein is for the purpose of describing particular aspects only and, unless specifically defined herein, is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "biodegradable" refers to polymers that dissolve or degrade in vivo within a period of time that is acceptable in a particular therapeutic situation. This time is typically less than five years and usually less than one year after exposure to a physiological pH and temperature, such as a pH ranging from about 6 to about 9 and a temperature ranging from about 25° C. to about 38° C.

The term "packed bed apparatus" refers to any vessel containing packing material capable of creating an emulsion upon contact with two immiscible fluids.

The term "active agent" refers to any biological or chemical agent.

The term "microparticles" refers to particles having a diameter of typically less than 1.0 mm, and more typically between 1.0 and 250 µm (microns). The microparticles of the present invention include, but are not limited to, microspheres, microcapsules, microsponges, microgranules and particles in general, with an internal structure comprising a matrix of agent and excipient. Microparticles may also include nanoparticles.

The term "nanoparticles" refers to particles having a diameter of typically between about 20 nanometers (nm) and about 2.0 microns, more typically between about 100 nm and about 1.0 microns.

An "injection" is a preparation intended for parenteral administration. Injections include, but are not limited to, liquid preparations that are drug substances or solutions or suspensions thereof.

The term "controlled release" refers to control of the rate and/or quantity of biologically active molecules delivered according to the drug delivery formulations of the invention. The controlled release kinetics can be continuous, discontinuous, variable, linear or non-linear. This can be accomplished using one or more types of polymer compositions, drug loadings, inclusion of excipients or degradation enhancers, or other modifiers, administered alone, in combination or sequentially to produce the desired effect. "Controlled release" microparticles include, but are not limited to, "sustained release" microparticles and "delayed release" microparticles.

The term "sustained release" refers to releasing a biologically active agent into the body steadily, over an extended period of time. Sustained release formulations offer the ability to provide a subject with a biologically active agent over a time period greater than that achieved by a typical bolus administration of the biologically active agent. Sustained release microparticles may advantageously reduce the dosing frequency of a biologically active agent.

A "biologically active agent", "bioactive agent" "biologically active moiety" or "biologically active molecule" can be any substance which can affect any physical or biochemical properties of a biological organism, including but not limited to, viruses, bacteria, fungi, plants, animals, and humans. Biologically active molecules can include any substance intended for diagnosis, cure mitigation, treatment, or prevention of disease in humans or other animals, or to otherwise enhance physical or mental well being of humans or animals.

By "treating" is meant the medical management of a patient with the intent that a cure, amelioration, stasis or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

The term "syringability" refers to uptake and delivery of microparticles through a needle without substantial clumping of the particles or clogging of the needle.

"Subject" is used herein to refer to any target of administration. The subject can be a vertebrate, for example, a mammal. Thus, the subject can be a human. The term does not denote a particular age or sex. Thus, adult and newborn subjects, as well as fetuses, whether male or female, are intended to be covered. A "patient" refers to a subject afflicted with a disease or disorder and includes human and veterinary subjects.

Disclosed are compounds, compositions, and components that can be used for, can be used in conjunction with, and/or can be used in preparation for, the disclosed apparatus and methods. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent is specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Figure 1A:
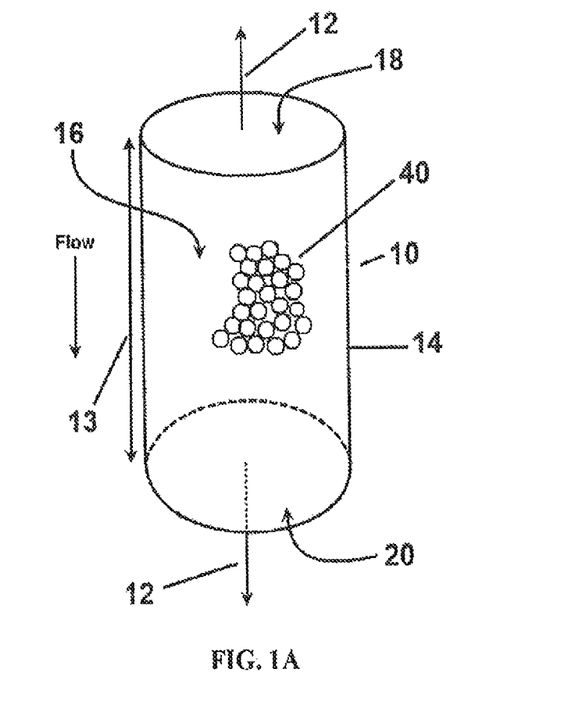
FIG. 1A is a perspective view of a column having an interior cavity, a longitudinal axis, and an inlet and outlet as described herein.
Figure 1B:
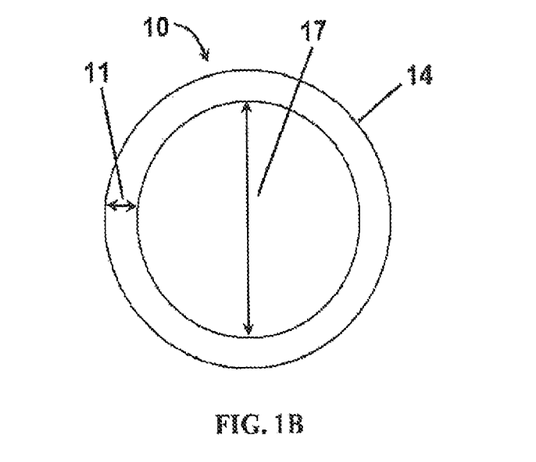
FIG. 1B is a top view of the column of FIG. 1A.

In a broad aspect of the invention, and with reference to FIGS. 1A and 1B, a column 10 for receiving a packing material 40 is disclosed. In one aspect, the column 10 can have a longitudinal axis 12 and a periphery 14 defining an interior cavity 16. In this aspect, the interior cavity 16 can have a longitudinal length 13. It is contemplated that the packing material 40 can be configured to permit fluid flow through the column 10 along the longitudinal axis 12. It is further contemplated that gaps formed within the packing material 40 inside the interior cavity 16 can function as channels which repeatedly cross paths as the fluid flows through the column 10.

In one aspect, it is contemplated that the column 10 can be a vessel of any shape capable of being filled with the packing material 40. For example, it is contemplated that the cross section of the column 10 can be substantially rectangular, square, round, or circular. In one exemplary aspect, as shown in FIGS. 1A and 1B, the interior cavity 16 of the column 10 can have a diameter 17, and the column can be substantially cylindrical. In another aspect, the longitudinal length 13 of the interior cavity 16 of the column 10 can range from about 1 cm to about 100 cm. In yet another aspect, the longitudinal length 13 of the interior cavity 16 of the column 10 can range from about 5 cm to about 20 cm.

In an additional aspect, the column 10 can comprise an inlet 18 in fluid communication with the interior cavity 16. It this aspect, the inlet 18 can be configured to receive at least one fluid. In an additional aspect, the column 10 can comprise an outlet 20 in fluid communication with the interior cavity 16. In one exemplary aspect, and as depicted in FIG. 1A, the outlet 20 can be spaced from the inlet 18 along the longitudinal axis 12 of the column 10.

In another aspect, and with reference to FIGS. 2A-5B, the column 10 can comprise at least one divider 50 positioned within the interior cavity 16. In this aspect, it is contemplated that each divider 50 of the at least one divider can extend along at least a portion of the longitudinal length 13 of the interior cavity 16. In a further aspect, the at least one divider 50 can be configured to partition the packing material 40 and direct fluid flow therethrough the interior cavity 16 of the column 10. It is contemplated that the at least one divider 50 can be configured to limit the formation of preferred pathways and static areas within the packing material 40 and to thereby maintain laminar flow therethrough the interior cavity 16 of the column 10. It is further contemplated that the at least one divider 50 can be scaled in a corresponding manner to the column 10 to provide similar benefits, regardless of the size of the column.

In an additional aspect, the at least one divider 50 can optionally be spaced from the inlet 18 of the column. In a further aspect, the at least one divider 50 can optionally be spaced from the outlet 20 of the column. In still a further optional aspect, the at least one divider 50 can be spaced from both the inlet 18 and the outlet 20 of the column.

Optionally, in one aspect, the at least one divider 50 can be secured thereto the periphery 14 of the column 10. Alternatively, in another aspect, the column 10 can further comprise an inlet screen attached to the inlet of the column and an outlet screen attached to the outlet of the column, and the at least one divider can be secured thereto at least one of the inlet screen and the outlet screen.

Figure 4A:
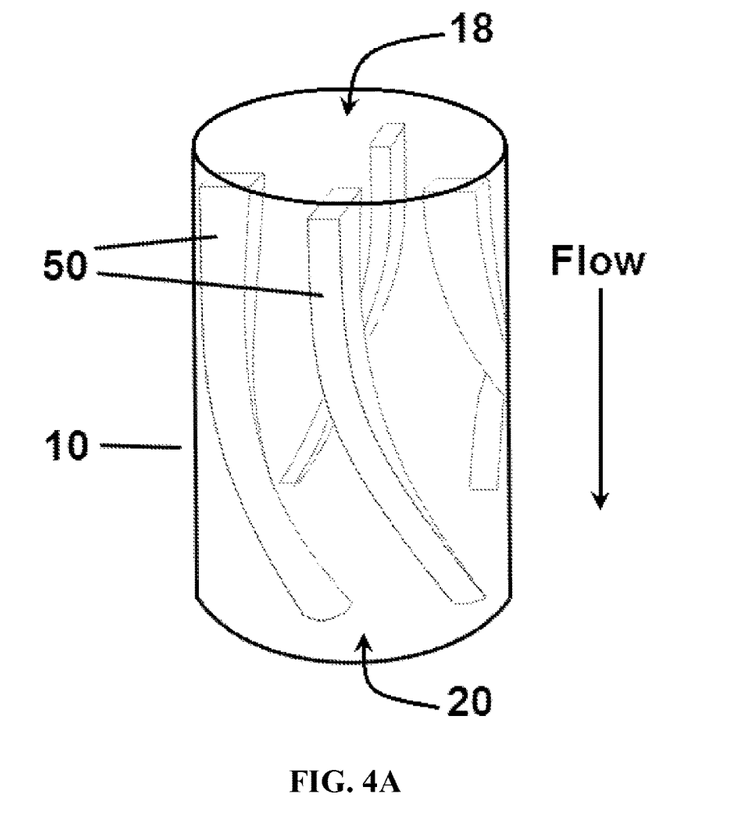
FIG. 4A is a perspective view of an exemplary column having dividers as described herein.
Figure 4B:
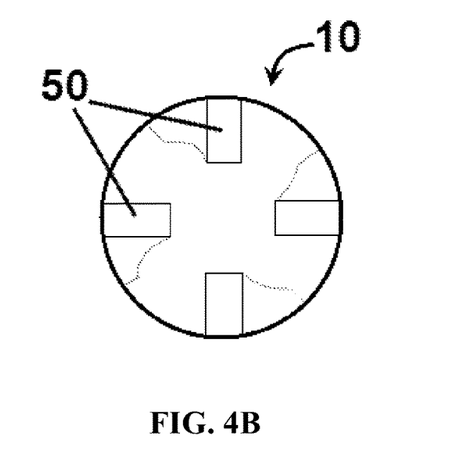
FIG. 4B is a top view into the interior cavity of the column of FIG. 4A.

In an additional aspect, the at least one divider 50 can comprise a plurality of dividers. In this aspect, it is contemplated that the plurality of dividers 50 can comprise two, three, four, five, six, seven, eight, nine, ten, eleven, twelve, or more dividers. In one aspect, as depicted in FIGS. 2A-4B, it is contemplated that each divider 50 of the plurality of dividers can extend inwardly from, or proximate to, the periphery 14 of the column 10 substantially orthogonally to the longitudinal axis 12 of the column. In a further aspect, at least two dividers 50 of the plurality of dividers can intersect within the interior cavity 16 of the column 10. In this aspect, it is contemplated that all of the plurality of dividers 50 can intersect within the interior cavity 16 of the column 10. In one exemplary aspect, as depicted in FIGS. 4A-4B, the plurality of dividers 50 can extend substantially helically along the longitudinal length 13 of the interior cavity 16 of the column 10.

It is contemplated that the at least one divider 50 can comprise materials that are similar or identical to the materials of the column 10. It is further contemplated that the at least one divider 50 can comprise materials that are similar or identical to the materials of the packing material 40. In some aspects, the column 10 and the packing material 40 can comprise different materials. However, it is also contemplated that the column 10 and the packing material 40 can comprise similar or identical materials.

Figure 2A:
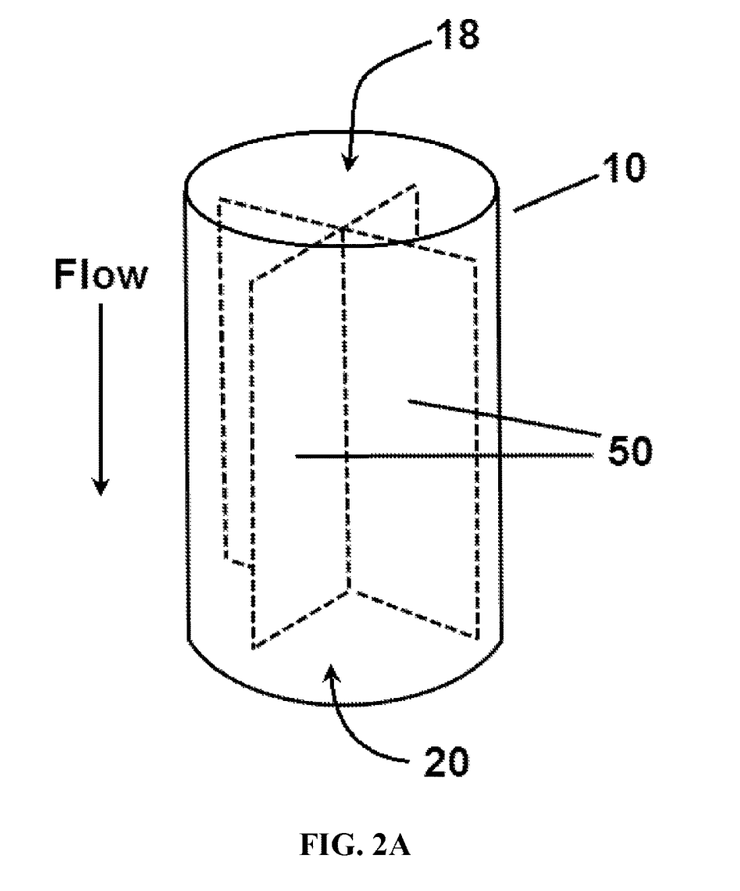
FIG. 2A is a perspective view of an exemplary column having dividers as described herein.
Figure 2B:
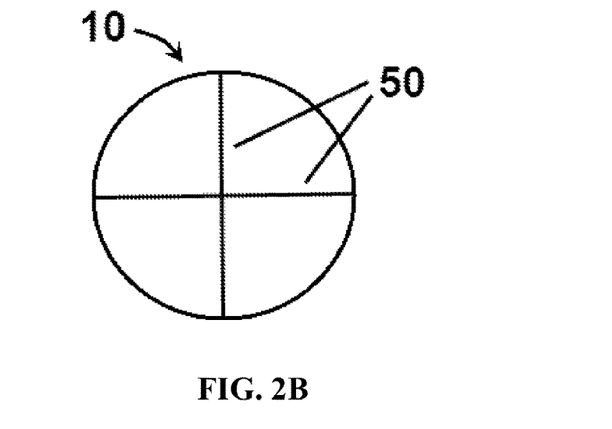
FIG. 2B is a top view into the interior cavity of the column of FIG. 2A.
Figure 2C:
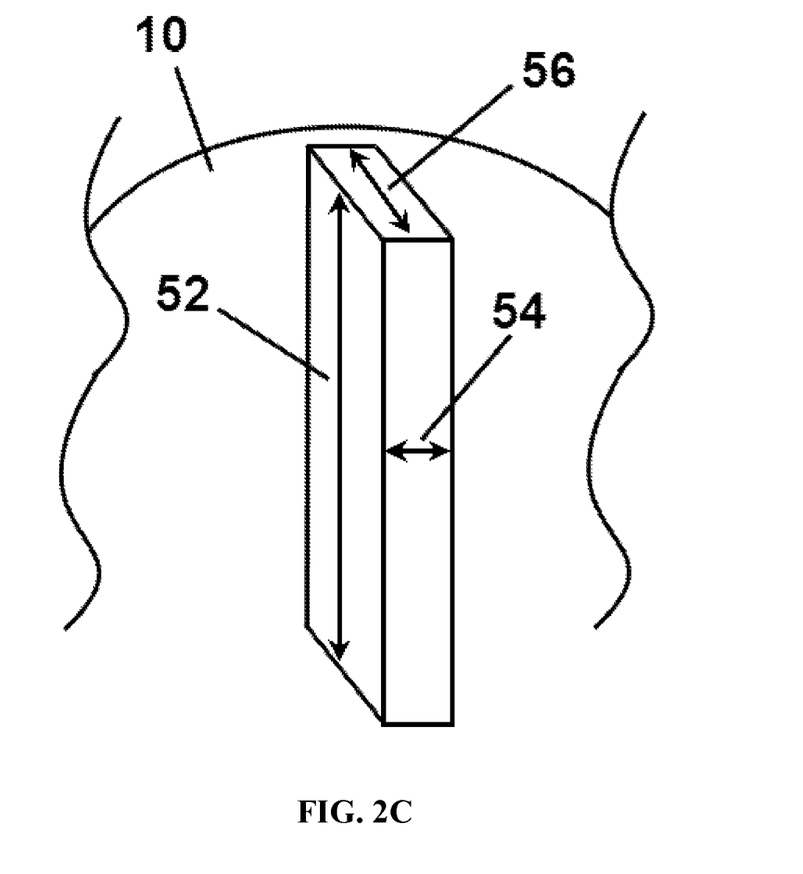
FIG. 2C is a close-up, partial cut-out view of a divider of FIG. 2A.
Figure 3A:
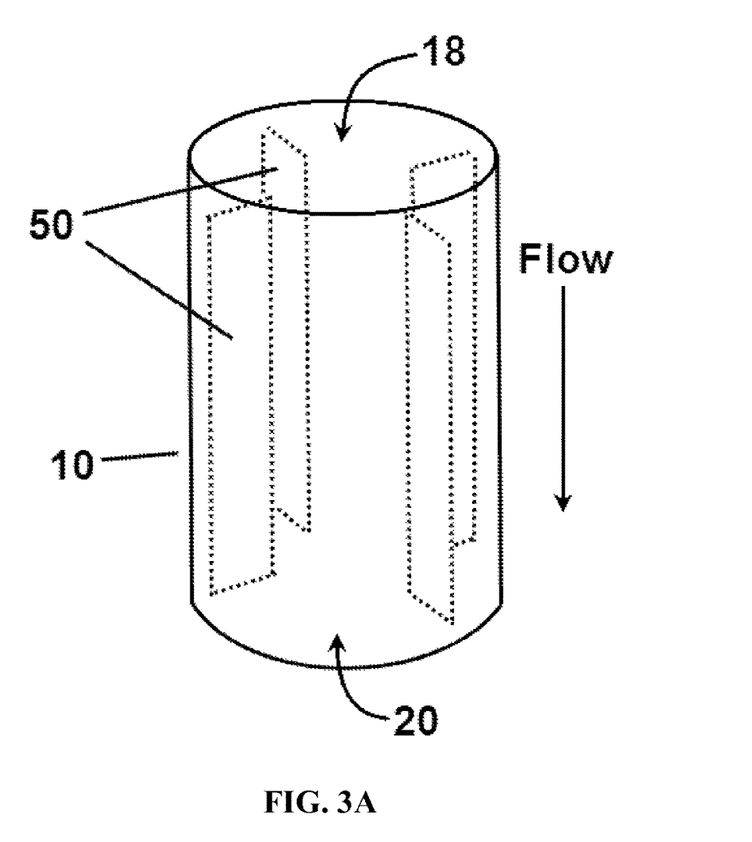
FIG. 3A is a perspective view of an exemplary column having dividers as described herein.
Figure 3B:
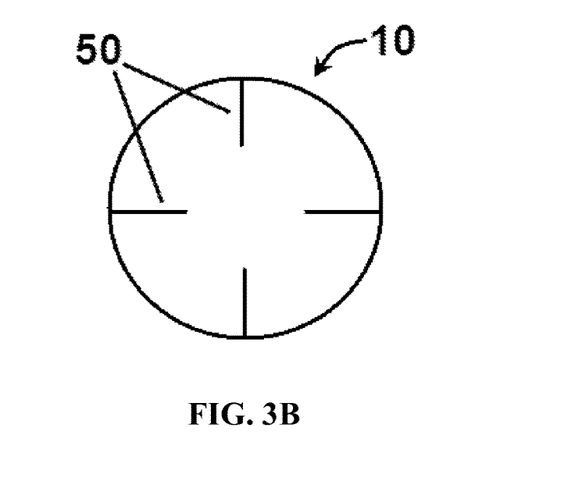
FIG. 3B is a top view into the interior cavity of the column of FIG. 3A.

In various aspects, and as depicted in FIG. 2C, each divider 50 of the at least one divider can have a longitudinal length 52, a width 54, and a thickness 56. In one exemplary aspect, as shown in FIG. 1B, it is contemplated that the periphery 14 of the column 10 can have a thickness 11, and the thickness of the periphery of the column can be substantially equal to the thickness 56 of each divider 50 of the at least one divider. In another exemplary aspect, the ratio of the longitudinal length 52 of each divider 50 to the longitudinal length 13 of the interior cavity 16 of the column 10 can range from about 0.1:1.0 to about 1.0:1.0, including 0.2:1.0, 0.3:1.0, 0.4:1.0, 0.5:1.0, 0.6:1.0, 0.7:1.0, 0.8:1.0, 0.9:1.0, and all ratios in between. In a further exemplary aspect, the ratio of the width 54 of each divider 50 to the diameter 17 of the interior cavity 16 of the column 10 can range from about 0.1:1.0 to about 1.0:1.0, including 0.2:1.0, 0.3:1.0, 0.4:1.0, 0.5:1.0, 0.6:1.0, 0.7:1.0, 0.8:1.0, 0.9:1.0, and all ratios in between.

In one exemplary and non-limiting aspect, the plurality of dividers 50 can comprise at least one divider extending along substantially the entire longitudinal length 13 of the interior cavity 16 of the column 10. In this aspect, it is contemplated that the plurality of dividers 50 can further comprise at least one divider extending along only a portion of the longitudinal length 13 of the interior cavity 16 of the column 10. In another exemplary and non-limiting aspect, the plurality of dividers 50 can be staggered along the longitudinal length 13 of the interior cavity 16 of the column 10.

Figure 5A:
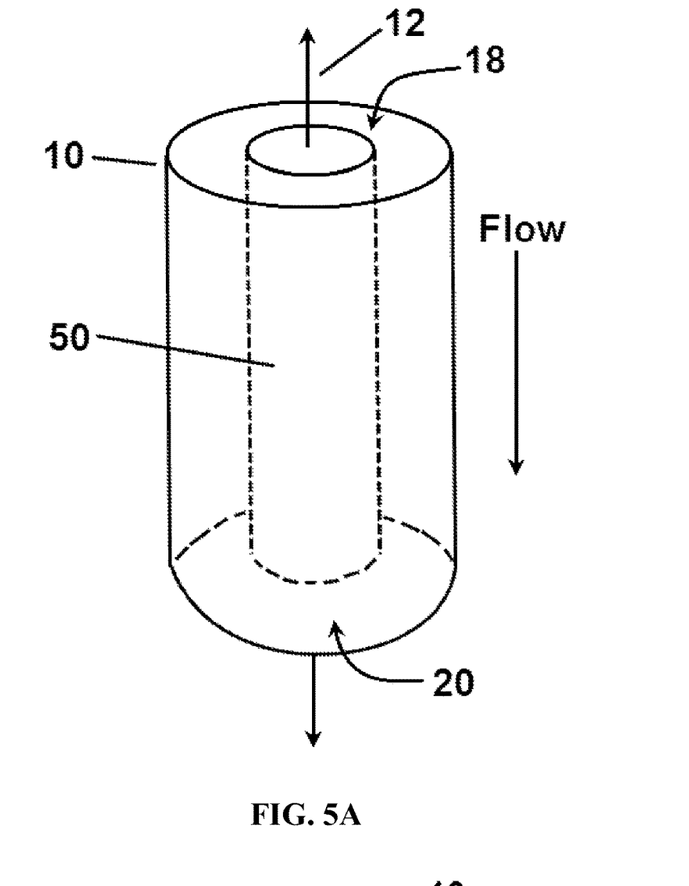
FIG. 5A is a perspective view of an exemplary column having cylindrical dividers as described herein.
Figure 5B:
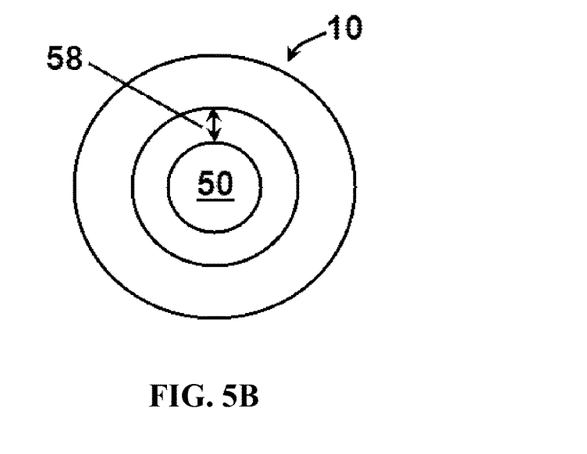
FIG. 5B is a top view into the interior cavity of the column of FIG. 5A.

In a further aspect, as shown in FIGS. 5A-5B, when the column 10 is substantially cylindrical, the at least one divider 10 can comprise at least one cylindrical divider 50 having a longitudinal axis and a diameter 58. In this aspect, the diameter 58 of each cylindrical divider 50 of the at least one cylindrical divider can be less than the diameter 17 of the interior cavity 16 of the column 10. It is contemplated that each cylindrical divider 50 can be secured within the interior cavity 16 of the column 10 such that the longitudinal axis of the cylindrical divider is substantially aligned with the longitudinal axis 12 of the column 10. It is further contemplated that the longitudinal axis of the at least one cylindrical divider 50 can coincide with, and be common with, the longitudinal axis 12 of the column 10.

In one exemplary aspect, and with reference to FIGS. 5A and 5B, the at least one cylindrical divider 50 can comprise a plurality of cylindrical dividers having incrementally decreasing diameters. In this aspect, the plurality of cylindrical dividers 50 can be secured within the interior cavity 16 such that the cylindrical dividers are radially spaced from one another relative to the longitudinal axis 12 of the column.

In another exemplary aspect, it is contemplated that the at least one divider 50 can comprise at least one cylindrical divider and at least one divider extending inwardly from the periphery 15 of the column 10, as described herein.

In one aspect, the packing material 40 can comprise at least one of metal, ceramics, plastic, and glass. In another aspect, the packing material 40 can be formed as at least one of conventional spheres, beads, pellets, chips, fibers, sponges, and pillows. In one exemplary aspect, the packing material 40 can be one of glass and a non-reactive metal, such as stainless steel. In another exemplary aspect, the packing material 40 can be one of boro-silicate glass beads and stainless steel beads. In a further aspect, when the packing material 40 comprises beads, the beads can have a diameter ranging from about 20 microns to about 2,000 microns. In yet another aspect, the beads can have a diameter ranging from about 50 microns to about 1,000 microns. In still another aspect, the beads can have a diameter ranging from about 300 microns to about 800 microns.

In operation, the disclosed columns can be employed in a method of preparing an emulsion. In one aspect, the method comprises positioning a packing material within the column. In another aspect, the method comprises introducing a plurality of fluids through the inlet of the column. In this aspect, it is contemplated that the plurality of fluids can combine within the interior cavity of the column to form an emulsion product. In a further aspect, the method comprises collecting the emulsion product through the outlet of the column. As used herein, the term "emulsion product" can refer to any emulsion resulting from the mixture of the plurality of fluids, including emulsions comprising a continuous phase that surrounds a dispersed phase containing active agents. In an exemplary non-limiting aspect, the emulsion product can comprise a dissolved active agent in the dispersed phase. In another exemplary non-limiting aspect, the emulsion product can comprise a suspended active agent in the dispersed phase. In a further exemplary non-limiting aspect, the emulsion product can comprise a dispersed active agent in the dispersed phase. In one aspect, it is contemplated that the emulsion product can comprise a microsuspension containing the active agent.

In exemplary aspects, it is contemplated that the plurality of fluids can comprise a first phase and a second phase. The first and second phases of the plurality of fluids can be any two fluids that are immiscible with one another. In one aspect, it is contemplated that the first phase can serve as a dispersed phase while the second phase can serve as a continuous phase that surrounds the first phase. If a third phase is utilized in the production of microparticles, the resulting product from the first and second phases is combined with the third phase. In this case, the product from the combination of the first and second phases and the third phase can be any two fluids that are immiscible with one another.

In these aspects, it is contemplated that the first phase can comprise a solvent and an active agent. Solvents for the first phase may be any organic or aqueous solvents. Examples of solvents include, but are not limited to, water, methylene chloride, chloroform, ethyl acetate, benzyl alcohol, diethyl carbonate, methyl ethyl ketone and mixtures of the above. In an exemplary aspect, the solvent is ethyl acetate or methylene chloride. In one aspect, the first phase can comprise a solution of a biodegradable polymer and a biological or chemical agent as a solution or suspension. Alternatively, it is contemplated that the biological or chemical agent can be dissolved or suspended in the second phase.

It is further contemplated that the second phase can comprise a solvent. The solvent for the second phase can be any organic or aqueous fluid that is immiscible with the first phase. Examples include, but are not limited to, water, a water-based solution, an organic solvent, and the like. In one exemplary aspect, the second phase can contain water, an emulsion stabilizer and, optionally, a solvent. In another exemplary aspect, the second phase can contain water, one or more biological or chemical agents and, optionally, a water-soluble polymer. In yet another exemplary aspect, the second phase can contain a second organic solvent, one or more biological or chemical agents, and a polymer.

It is still further contemplated that, when a third phase is used within the scope of the disclosed methods, the third phase can comprise a solvent. In one aspect, the solvent of the third phase can be any organic solvent or water.

In one aspect, the solvents of the first phase and the second phase can be selected from the group consisting of methylene chloride, chloroform, ethyl acetate, benzyl alcohol, diethyl carbonate, methyl ethyl ketone, and water.

Active agents of the invention can be any biological or chemical agent. Examples of biologically active agents include, but are not limited to, antibodies, peptides, proteins, enzymes, fusion proteins, porphyrins, nucleic acids, nucleosides, oligonucleotides, antisense oligonucleotides, RNA, DNA, siRNA, RNAi, aptamers, and small molecule drugs. Other biologically active agents include, but are not limited to, dyes, lipids, cells, and viruses. Biological agents of use in the invention may be any agent capable of having an effect when administered to an animal or human. In one aspect, they include, but are not limited to, an organic molecule, an inorganic molecule, antiinfectives, cytotoxics, antihypertensives, antifungal agents, anti-anxiety agents, anti-inflammatory agents, anti-tumor agents, anti-tubulin agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, blood clotting factors, hemopoietic factors, cytokines, interleukins, colony stimulating factors, growth factors, growth factor analogs, fragments thereof and the like. In another aspect, biological agents include PEGylated bioactive agents. In an additional aspect, a biologically active molecule is conjugated to a non-toxic, long-chain, hydrophilic, hydrophobic or amphiphilic polymer. In a further aspect, a bioactive agent such as insulin is conjugated to polyethylene glycol.

Exemplary chemical agents can be any synthetic or natural agent, including, for example and without limitation, antioxidants, porosity enhancers, solvents, salts, cosmetics, food additives, textile-chemicals, agro-chemicals, plasticizers, stabilizers, pigments, opacifiers, adhesives, pesticides, fragrances, antifoulants, dyes, oils, inks, catalysts, detergents, curing agents, flavors, foods, fuels, herbicides, metals, paints, photographic agents, biocides, pigments, plasticizers, propellants, solvents, stabilizers, polymer additives and the like.

Thus, it is contemplated that the active agent of the first phase can be selected from the group consisting of antioxidants, porosity enhancers, solvents, salts, cosmetics, food additives, textile-chemicals, agro-chemicals, plasticizers, stabilizers, pigments, opacifiers, adhesives, pesticides, fragrances, antifoulants, dyes, salts, oils, inks, cosmetics, catalysts, detergents, curing agents, flavors, foods, fuels, herbicides, metals, paints, photographic agents, biocides, pigments, plasticizers, propellants, solvents, stabilizers, polymer additives, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors, growth factor analogs, and fragments thereof. In one aspect, it is contemplated that the emulsion product can comprise a microsuspension containing microparticles as described herein. In this aspect, it is further contemplated that the microsuspension of the emulsion product can contain the active agent of the first phase.

In an additional aspect, the second phase can further comprise an emulsion stabilizer. It is optionally contemplated that the first phase can comprise an emulsion stabilizer. It is contemplated that the emulsion stabilizer can be selected from the group consisting of poly(vinyl alcohol), polysorbate, protein, and poly(vinyl pyrrolidone). In one aspect, the concentration of the emulsion stabilizer can range from about 0% to about 20% of either or both of the first phase and the second phase. In another aspect, the concentration of the emulsion stabilizer can range from about 0.5% to about 5% of either or both of the first phase and the second phase.

In a further aspect, at least one of the first phase and the second phase can comprise a polymer, such as, for example and without limitation, a biodegradable polymer. In this aspect, it is contemplated that the polymer can be selected from the group consisting of poly(d,l-lactic acid), poly(l-lactic acid), poly(glycolic acid), poly(d,l-lactide-co-glycolide) (PLGA), poly(caprolactone), poly(orthoesters), poly(acetals), and poly(hydroxybutryate). In exemplary aspects, when the polymer is PLGA, it is contemplated that the polymer can have a monomer ratio of lactide:glycolide ranging from about 40:60 to about 100:0. In one aspect, it is contemplated that the polymer can have a monomer ratio of lactide:glycolide ranging from about 45:55 to about 100:0. In another aspect, the polymer can comprise block copolymers of hydrophilic and hydrophobic polymers. In an additional aspect, it is contemplated that the inherent viscosity of the polymer can range from about 0.1 to about 2.0 dL/g. In yet another aspect, it is contemplated that the inherent viscosity of the polymer can range from about 0.1 to about 1.0 dL/g, including, for example and without limitation, 0.15 dL/g, 0.30 dL/g, 0.60 dL/g, and 0.90 dL/g. In still a further aspect, it is contemplated that the concentration of the polymer in the first and/or the second phase can range from about 1% to about 50% w/w. In yet another aspect, it is contemplated that the concentration of the polymer in the first and/or the second phase can range from about 5% to about 20% w/w.

More particular descriptions of exemplary methods for producing emulsions are set forth below. In one aspect, the method for producing an emulsion for microparticle production includes (1) forming a first phase typically containing an organic solvent, a polymer, and one or more biologically active agents and/or chemicals; (2) forming a second phase typically containing water as the second solvent, an emulsion stabilizer and optionally a solvent; and (3) passing the first and second phases through the column to form an "oil in water" type emulsion.

In another aspect, the method for production of an emulsion includes (1) forming a first phase typically containing an organic solvent and an emulsion stabilizer; (2) forming a second phase typically containing water as the second solvent, one or more biologically active agents and/or chemicals, and a water soluble polymer; and (3) passing the first and the second phases through the column to form a "water in oil" type emulsion.

In a third aspect, the invention provides methods for producing emulsions by (1) forming a first phase containing an organic solvent and, optionally, an emulsion stabilizer; (2) forming a second phase containing a second organic solvent, one or more biologically active agents and/or chemicals, and a polymer; and (3) passing the first and the second phases through the column to form an organic emulsion.

In yet another aspect, the invention provides methods for producing emulsions by (1) forming a first phase typically containing water, one or more biologically active agents and/or chemicals and an emulsion stabilizer; (2) forming a second phase typically containing an organic solvent and a polymer; (3) forming a third phase typically containing water and optionally containing a stabilizer; (4) passing the first and the second phases through a first column to form a "water in oil" type emulsion; and (5) passing the first emulsion and the third phase through a second column to form a "water in oil in water" emulsion.

It is contemplated that the use of the disclosed columns to create an emulsion provides for uniform droplets and resultant microparticle size distribution, as well as conditions suitable for many chemical or biological agents. Additionally, it is contemplated that the apparatus and methods of the invention can easily produce scalable results. It is further contemplated that desirable batches of microparticles produced in the laboratory on a small scale can easily be reproduced on a larger manufacturing scale merely by utilizing the same packing material in a column with a larger diameter. Therefore, it is contemplated that the column permits inexpensive and efficient scaling of the production process once the desired microparticles are produced on a small scale in the laboratory.

In an exemplary aspect, the methods of the invention provide a continuous process for making an emulsion for microparticle production in a wide range of flow rates and volumes. In some aspects, the methods involve a process for making microparticles with a pre-determined size distribution. In alternative aspects, the methods provide a continuous process for making microparticles at very low flow rates.

The columns and methods of using the columns to produce microparticles are not dependent on turbulent flow. Rather, the methods of making microparticles of the present invention work at laminar flow rates. It is contemplated that microparticles with a narrow and repeatedly precise particle size distribution can be produced using the disclosed methods. Additionally, it is contemplated that the microparticles can be produced on a small scale and easily scaled-up to manufacturing size by merely altering the diameter of the column.

Through application of the disclosed methods, the emulsions are made as the two fluids, or phases (typically oil and water), are flowing through the gaps inside the packing material. As the two phases are flowing through the bed of packing material, they cross each other's path repeatedly, and the continuous phase (usually the water) divides the discontinuous phase (usually the oil) into droplets, thus creating an emulsion. The discontinuous phase droplet size is reduced repeatedly until a final droplet size is achieved. Once the discontinuous droplets have reached a certain size, they will not be reduced any further even if they continue flowing through the packing material. The disclosed methods permit formation of a precisely sized emulsion at laminar flow conditions.

The very unique dynamics of the packing material allow for the continuous production of microparticles at very low flow rates. These low flow rates permit consistent production of high-quality microparticles in batches as small as 0.1 grams that maintain consistent particle size distribution. Additionally, these unique flow dynamics also provide for scalability from laboratory to manufacturing sized batches.

The disclosed columns and methods of using the columns provide an emulsion-based process for making microparticles that is insensitive to flow rates within the laminar flow region. Unlike turbulent mixer-based processes, the methods of the invention are not sensitive to changes in the flow rates when operated within a laminar flow region. The flow rate of use in the invention can be any laminar flow rate. In one exemplary aspect, the flow rate of the fluids through the column can range from about 10 ml/minute to about 50 liters/minute. In another exemplary aspect, the flow rate of the fluids through the column can range from about 20 ml/minute to about 5 liters/minute.

The disclosed columns and methods of using the columns provide an emulsion-based process for making microparticles that is easily scalable from laboratory to manufacturing sized batches. A typical batch may demonstrate 10.000-fold scalability. In a particular batch, the size of the batch may be chosen from one or more of, but not limited to, 0.1 gram, 1 gram, 10 grams, 50 grams, 100 grams, 250 grams, 0.5 kilograms, 1 kilogram, 2 kilogram, 5 kilograms, 10 kilograms, 15 kilograms, 20 kilograms, 25 kilograms, 30 kilograms, and the like. One method of increasing the scale of a batch of microparticles is to increase the diameter of the vessel. Such increase will function to increase the volume of emulsion through the vessel, thus directly increasing the size of the batch produced.

The disclosed columns and methods of using the columns provide an emulsion-based process for making microparticles that provides for tight control of the particle size distribution. Microparticle size distribution may be manipulated by altering the packing material size, shape and type; rearranging the inlet or outlet enclosures; alteration of the physical properties of the first, second or third phases; altering the length or diameter/width of the column and the like. For example, the final microparticle size can be determined by the size of the packing material, such as the diameter of a glass bead. Additionally, it is contemplated that the length of the column can directly affect the particle size distribution.

It is contemplated that the phases can be introduced into the column by any method. In one aspect, the phases are introduced through pipes or tubes and can be pumped, forced by gas or another type of pressure source, fed by gravity, or pulled by a vacuum in communication with the inlet of the column. The liquid phases can be carried by pipes comprising stainless steel, glass or plastic compatible with the solvents and temperatures used. The fluid phases may be at ambient temperature or at any temperature required between approximately freezing and approximately boiling for the particular fluid. It is contemplated that the disclosed column and methods of using the disclosed column can be utilized at any pressure compatible with the equipment utilized. It is further contemplated that the pressure can be adjusted to a pressure necessary to overcome the resistance of the packing material and to provide a flow rate in the laminar flow region of the column.

Microparticles containing a biological or chemical agent are collected from the emulsion product of the packed bed apparatus via solvent extraction. Such techniques are known in the art. Solvent extraction can be done by, but is not limited to, the methods of spray drying, extraction into a water or other liquid bath, freeze-drying, evaporation and the like.

Figure 6:
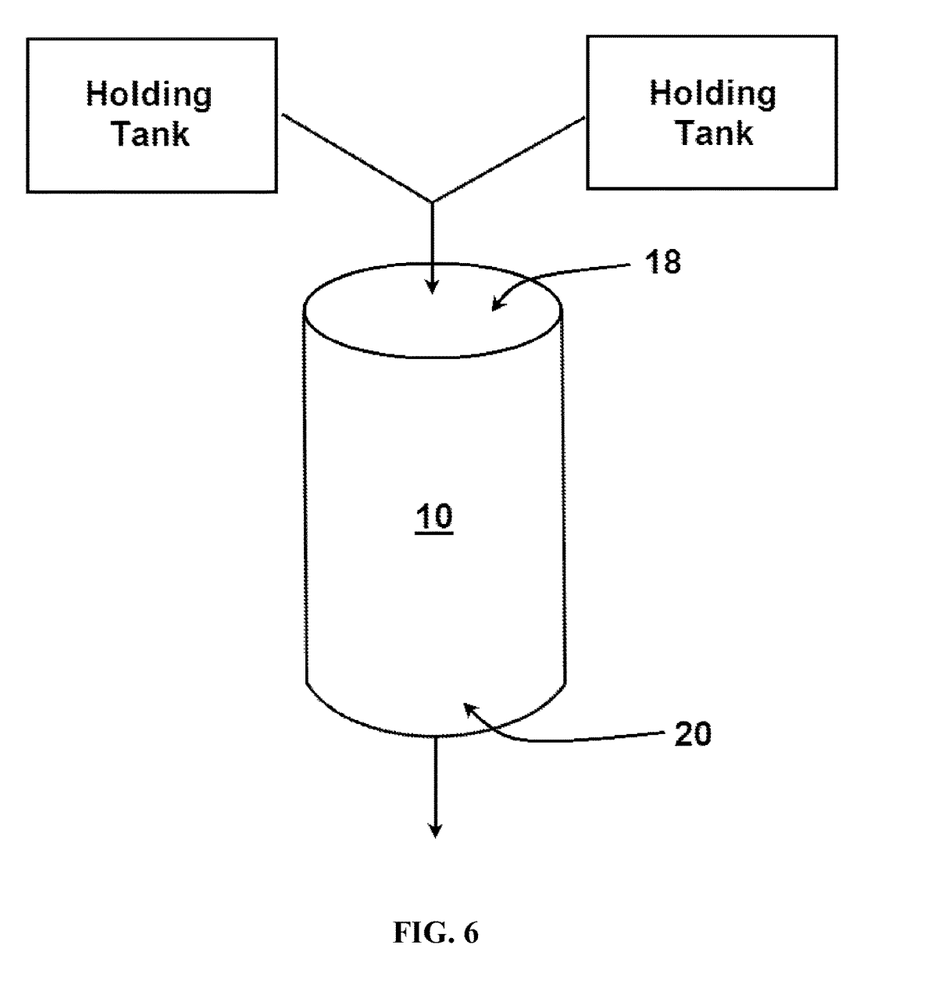
FIG. 6 is a schematic diagram of an exemplary packed bed apparatus as described herein.

In various aspects, as depicted schematically in FIG. 6, the disclosed columns 10 can be employed as part of a packed bed apparatus. In one exemplary aspect, the packed bed apparatus can comprise one or more conventional holding tanks or feed vessels for holding the first or second phases. The holding tanks or feed vessels can be jacketed or otherwise equipped to provide temperature control of the first or second phases. A tube may run from each holding tank or feed vessel through a pump and later merge with the tube from other holding tanks or feed vessels proximate the inlet 18 of the column 10. Additionally, it is contemplated that the packed bed apparatus can include pumps or other means of moving the phases into and through the column 10. In some aspects, the phases can flow from the holding tanks or feed vessels into the column 10 without pumps, by simple gravity, by pressure, or by a vacuum from the other end of the packed bed apparatus, and the like. The tubes can further include addition of flow meters, feedback control, flow rate programming via programmed logic control, and the like.

It is contemplated that the disclosed methods are functional at any temperature within the operating range of the equipment, solvents and active agents. Factors that determine the appropriate temperature for a particular process include the optimum temperature for the two phases to be transported through the column. If a third phase is utilized, it is contemplated that the temperature of the first column can be the same or different than that of the second column. It is further contemplated that the temperature needs to be such that the two phases are maintained at a desirable viscosity. Additionally, the solubility of the polymer and active molecule can require an increase in temperature in order to produce a complete solution. The temperature can additionally be affected by the stability limit of any biological or chemical agents present in the various phases. In various aspects, typical operating temperatures can range from about 0 to 50 degrees Celsius. In one aspect, typical operating temperatures can range from about 10 to about 40 degrees Celsius. In another aspect, typical operating temperatures can range from about 15 to about 30 degrees Celsius. In yet another aspect, typical operating temperatures can range from about 18 to about 25 degrees Celsius.

It is contemplated that the microparticles produced by the disclosed methods can be used for any purpose. In one aspect, they are administered to a subject. In this aspect, it is contemplated that they can be administered to subjects in single or multiple doses. It is further contemplated that the microparticles can also be administered in a single dose form that functions to further release the biological or chemical agent over a prolonged period of time, eliminating the need for multiple administrations.

It is further contemplated that the microparticles produced by the disclosed methods can be stored as a dry material. In the instance of administration to a subject, prior to such use, the dry microparticles can be suspended in an injection vehicle. Upon suspension, the microparticles can then be injected into the subject or otherwise utilized.

As used herein, an injection vehicle ("diluent", "injection medium", "injection solution", "pharmaceutical liquid vehicle", "suspension medium", "excipient", "carrier") is an aqueous or non-aqueous liquid for suspending and injecting microparticles. Aqueous injection vehicles comprise water and at least one of a buffer, salts, non-ionic tonicity compounds, viscosity enhancers, stabilizers, antimicrobials, and surfactants. In one aspect, the microparticles can be suspended in an injection solution comprising SDS, Tween 20 or mannitol. In one exemplary aspect, the injection vehicle can be 0.5%-2.5% sodium carboxymethylcellulose in water. In another exemplary aspect, the injection vehicle can be 0-1.5% (w/w) sodium carboxymethylcellulose, 0-0.5% (w/w) Tween-80 or Tween-20, 0-330 mM NaCl, 0-10 mM sodium phosphate in water, pH 5-9. In another aspect, it is contemplated that the microparticles can be suspended in an injection solution comprising 0.5% SDS. In a further aspect, it is contemplated that the injection vehicle can comprise 0.2% Tween-20 in water.

It is contemplated that microparticles can vary in size, ranging from submicron to millimeter diameters. Microparticle size is partially determined by the size and shape of individual packing material particles within the column. Large and misfit packing materials generally pack together less closely than smaller packing material particles and produce larger gaps for the fluids to flow through. Thus, it is contemplated that larger gaps in the packing material produce larger microparticles and smaller gaps in the packing material produce smaller microparticles. It is further contemplated that the flow rate does not affect the size of the microparticles produced from a particular column. In one aspect, it is contemplated that the diameters of the microparticles produced by the disclosed methods can range from about 1 micron to about 200 microns, thereby facilitating administration to a subject through a syringe needle. In another aspect, the diameters of the microparticles produced by the disclosed methods can range from about 10 microns to about 100 microns. In an additional aspect, the diameters of the microparticles can be less than about 90 microns. In an exemplary aspect, the diameters of the microparticles produced by the disclosed methods can range from about 25 microns to about 125 microns. In another exemplary aspect, the diameters of the microparticles can range from about 25 microns to about 80 microns. In a further aspect, the microparticles produced by the disclosed methods can have a mean diameter ranging from about 25 microns to about 80 microns. In yet another aspect, the microparticles can have a mean diameter ranging from about 10 microns to about 50 microns. In one exemplary aspect, the diameters of the microparticles produced by the disclosed methods can be less than or equal to about 75% of the inner diameter of a needle to be used to inject the microparticles into a subject. In another aspect, the diameters of the microparticles can be less than or equal to about 50% of the inner diameter of the needle. In yet another aspect, the diameters of the microparticles can be less than or equal to about 35% of the inner diameter of the needle. In still another aspect, the diameters of the microparticles can be less than or equal to 25% of the inner diameter of the needle. In still another aspect, the diameters of the microparticles can be less than or equal to 10% of the inner diameter of the needle.

For medical applications, it is contemplated that the diameter of the microparticles produced by the disclosed methods can range from about 1 micron to about 200 microns. In another aspect, it is contemplated that the diameter of the microparticles can range from about 1 micron to about 100 microns. In yet another aspect, it is contemplated that the diameter of the microparticles can range from about 10 microns to about 50 microns. Microparticle size distribution can be measured by several methods including, but not limited to, laser light diffraction, scanning electron microscopy, visible light microscopy, and conventional electrical sensing zone methods. The results can be expressed as an average (mean or mode) value, a standard deviation or half width, the diameters below which 10%, 50% and 90% of the particles are found ($d_{10}$, $d_{50}$, $d_{90}$), and the fraction of the microparticles within a given range, among others. Further, data can be expressed by volume weighted or number weighted statistics. For the instant description, laser diffraction measurements are used, volume weighted statistics are employed, the average is expressed as a mean value, and $d_{10}$, $d_{50}$, $d_{90}$, etc., as well as a fraction within a range, are used to describe particle size distributions.

It is contemplated that the use of the disclosed columns to form microparticles can provide a narrow size distribution centered at a desired mean diameter with most of the particles contained in a desired range. During the final steps of microparticle manufacturing, filtration is typically used to exclude particles with diameters lower or higher than the desired cutoffs. With traditional microparticle manufacturing involving turbulent mixing, the particle size distribution is broad, and the yield in a narrow range can be too low to be economical so that a wide particle size range is necessitated. Through use of the disclosed columns, operated as described, it is contemplated that narrow particle size distributions can be obtained, and final filtration (sieving) to achieve the desired cutoff diameters can produce a high yield of microparticles. It is further contemplated that the narrow particle size distribution obtained through use of the disclosed columns can lead to more effective syringing of the microparticles through small needles.

In some aspects, the diameters of the microparticles produced using the disclosed methods can range from about 1 micron to about 6 microns. In other aspects, the diameters of the microparticles produced using the disclosed methods can range from about 10 microns to about 25 microns. In still other aspects, the diameters of the microparticles produced using the disclosed methods can range from about 25 microns to about 80 microns. In an exemplary aspect, the microparticles can have an average diameter of less than about 45 microns. In yet another aspect, the microparticles have an average diameter of about 30 microns. In a further aspect, the diameter of the microparticles can range from about 10 microns to about 30 microns. In still a further aspect, greater than about 80% of the microparticles can have a diameter ranging from about 25 to about 63 microns. In still another aspect, greater than about 90% of the microparticles can have a diameter ranging from about 25 microns to about 63 microns.

In one aspect, it is contemplated that the microparticles can be of a suitable size and morphology to allow for delivery though a needle having a small inner-diameter, such as a 25 gauge needle or narrower. Microparticles are referred to herein as "syringable" if they are able to be taken up and delivered though a needle without substantial clumping of the microparticles or clogging of the needle. In one exemplary aspect, the microparticles are syringable through a 25 gauge needle or narrower. Microparticles are referred to herein as "injectable" if they consistently can be injected into a desired locus of a subject though a needle. In one exemplary aspect, the microparticles are injectable through a 25 gauge needle or narrower.

In one aspect particularly suited for medical applications, the microparticles can be syringable through a needle having a gauge of at least 25 and having a nominal inner diameter of 0.0095 inches (241 microns) or less. In another aspect, the microparticles can be syringable through a needle having a gauge of at least 27 and having a nominal inner diameter of 0.0075 inches (190 microns) or less. In an additional aspect, the microparticles can be syringable through a needle having a gauge of at least 29 and having a nominal inner diameter of 0.0065 inches (165 microns) or less. In a further aspect, the microparticles can be syringable through a needle having a gauge of at least 30 and having a nominal inner diameter of 0.0055 (140 microns) inches or less. In an exemplary aspect, when suspended in an injection vehicle at a concentration ranging from about 50 mg/ml to about 600 mg/ml, the microparticles can be syringable through a needle having a gauge of 25, 27, 29 or 30. In another exemplary aspect, when suspended in an injection vehicle at a concentration ranging from about 50 mg/ml to about 200 mg/ml, the microparticles can be syringable through a needle having a gauge of 25, 27, 29 or 30. In a further exemplary aspect, when suspended in an injection vehicle at a concentration ranging from about 100 mg/ml to about 600 mg/ml, the microparticles can be syringable through a needle having a gauge of 25 or 27.

In one aspect, it is contemplated that the microparticles produced by the disclosed methods can flow freely without the formation of aggregates and can be readily suspended in an injection vehicle for injection. It is contemplated that free-flowing and/or un-agglomerated powders are advantageous because they roll with substantially no friction and can be easily placed in containers and/or suspended or incorporated into a solution suitable for injection. Flowability of microparticles can be measured by any suitable means such as a Jenike Shear Tester (Jenike & Johanson, Inc., Westford, Mass.), which measures the direct shear strength of powders and other bulk solid materials. Using a Jenike Shear Tester, a shear cell (base and ring) is filled with material; a vertical load is applied to the covered cell, using weights and the weight carrier; and the shear cell ring is pushed horizontally across the base, with the required force measured and recorded. Other apparatuses for measuring flowability include a powder rheometer (Freeman Technology, Worcestershire, UK) that measures the force of a twisted blade along a helical path through a powder sample, thereby establishing a required flow rate and pattern of flow. A critical orifice and an angle of repose using an avalanche process may also be measured.

It is contemplated that the microparticles produced using the disclosed methods can have a core load sufficient to deliver a biologically active agent to maintain therapeutically effective levels of the biologically active agent for sustained periods. In exemplary aspects, the microparticles can have a core load ranging from about 2.5% to about 90% by weight of the biologically active agent. In one aspect, the microparticles can have a core load of greater than or equal to about 5% by weight of the biologically active agent. In another aspect, the microparticles can have a core load of greater than or equal to about 10% by weight of the biologically active agent. In an additional aspect, the microparticles can have a core load of greater than or equal to about 15% by weight of the biologically active agent. In a further aspect, the microparticles can have a core load of greater than or equal to about 20% by weight of the biologically active agent. In still a further aspect, the microparticles can have a core load of greater than or equal to about 30% by weight of the biologically active agent.

In exemplary aspects, it is contemplated that the microparticles produced using the disclosed methods can be configured to release a biologically active agent over a period of at least about 1 month to about 12 months. In one aspect, the microparticles can be configured to release a bioactive agent over a period of at least about 3 months to about 6 months. In another aspect, the microparticles can be configured to release a bioactive agent over a period of about 1 week to about 3 months.

It is well known in the art that biodegradable polymer compositions can be varied to affect the sustained release duration of a given composition. For example PLGA with a 45:55 lactide:glycolide ratio and an inherent viscosity of 0.15 dL/g can release drug over a one to two week period. The high glycolide content and low molecular weight, reflected by the relatively low inherent viscosity value, lead to rapid hydrolysis of the polyester chains with consequent drug release. On the other hand, 85:15 lactide:glycolide PLGA, with an inherent viscosity of 0.91, reflecting a molecular weight of over 100,000 daltons, gives a much longer drug release profile that can last more than 6 months.

In one aspect, it is contemplated that the microparticles produced using the disclosed methods can have high encapsulation efficiency. It is further contemplated that the microparticles can have an encapsulation efficiency of greater than or equal to about 80%. In another aspect, the microparticles can have an encapsulation efficiency of greater than or equal to about 90%. In yet another aspect, the microparticles can have an encapsulation efficiency of greater than or equal to about 95%. In still another aspect, the microparticles can have an encapsulation efficiency of about 100%.

In another aspect, it is contemplated that the microparticles produced by the disclosed methods can have any suitable morphology. In one aspect, the microparticles can be solid. In an additional aspect, the microparticles can be smooth or non-pitted. In a further aspect, the microparticles can be homogenous or monolithic. In still a further aspect, it is contemplated that the microparticles can have a morphology allowing for a high core load, high encapsulation efficiency, low burst, sustained release, and syringability.

It is contemplated that the microparticles produced using the disclosed methods can be administered to a patient in need of treatment by injection, nasal, pulmonary, oral, vaginal or other means of delivery. In one aspect, the disclosed methods can be used to deliver a biologically active agent to any desired site, including, but not limited to, intramuscular, intradermal, subcutaneous, intraorbital, intraocular, intravitreal, intraaural, intratympanic, intrathecal, intracavitary, peritumoral, intratumoral, intraspinal, epidural, intracranial, and intracardial sites of a patient.

It is contemplated that the microparticles produced by the disclosed methods can release a biologically active agent by any suitable means to allow for a controlled release of the biologically active agent. It is further contemplated that the microparticles can release the biologically active agent by bulk erosion, diffusion or a combination of both. It is still further contemplated that the microparticles can be easily suspendable and syringable while also being configured to provide increased duration, increased stability, decreased burst and controlled, sustained or delayed release of biologically active agents in vivo.

Optionally, a surfactant can be used in order to provide formulations that have the required syringability. In one exemplary aspect, a surfactant can be used to provide a stable emulsion during the process of forming the microparticles as disclosed herein. In another aspect, a surfactant can be used to prevent agglomeration during drying of the microparticles. In an additional aspect, a surfactant can be used to prevent agglomeration within the injection vehicle during the process of delivering the microparticles. It is contemplated that surfactants can provide batch-to-batch consistency of microparticles by forming a thin layer of material around the microparticles that helps prevent clumping. It is further contemplated that any suitable surfactant can be used for these purposes. Suitable surfactants include, but are not limited to, cationic, anionic, and nonionic compounds such as poly(vinyl alcohol), carboxymethyl cellulose (CMC), lecithin, gelatin, poly(vinyl pyrrolidone), polyoxyethylenesorbitan fatty acid ester (Tween 80, Tween 60, Tween 20), sodium dodecyl sulfate (SDS) and the like.

In one exemplary aspect, the microparticles can be formed using an emulsion comprising poly (vinyl alcohol). More particularly, the microparticles can be formed using an emulsion comprising 1.0% poly (vinyl alcohol). In various aspects, the concentration of surfactant in the process medium is established to be an amount sufficient to stabilize the emulsion.

In another exemplary aspect, the microparticles can be lyophilized in a solution comprising SDS, Tween 20 or mannitol. In one particular aspect, the microparticles can be lyophilized in a solution comprising 7.8% SDS.

In a further aspect, the disclosed methods can be used to produce microparticles comprising PEGylated insulin. It is contemplated that these microparticles can have a burst release in vivo and in vitro of less than 5%, a drug core load greater than 12% (w/w) and an encapsulation efficiency of greater than 80%. It is further contemplated that these microparticles can have a mean diameter of less than 45 microns, and greater than 90% (volume weighted) of the microparticles can have a diameter ranging from about 25 microns to about 63 microns. It is still further contemplated that the microparticles of this invention can be capable of injection into a subject through needles of 25, 27 and 29 gauge or narrower, whereby the insulin plasma level is maintained for about one week to about four weeks.

What is claimed is:
1. A method of preparing an emulsion, the method comprising:
positioning a packing material within a column, the column having a longitudinal axis and a periphery defining an interior cavity, the interior cavity having a longitudinal length; the packing material configured to permit fluid flow through the column along the longitudinal axis, the column comprising:
an inlet in fluid communication with the interior cavity;
an outlet in fluid communication with the interior cavity; and
at least one divider positioned within the interior cavity, each divider of the at least one divider extending along at least a portion of the longitudinal length of the interior cavity,
wherein the at least one divider is configured to partition the packing material and direct fluid flow therethrough the interior cavity;
introducing a plurality of fluids through the inlet of the column under laminar flow conditions, wherein the plurality of fluids combine within the interior cavity of the column to form an emulsion product; and
collecting the emulsion product through the outlet of the column;
wherein the method is insensitive to flow rates; and
wherein the column can be utilized at any pressure.

2. The method of claim 1, wherein the packing material comprises at least one of metal, ceramics, plastic, and glass.

3. The method of claim 2, wherein the packing material is formed as at least one of spheres, beads, pellets, chips, fibers, sponges, and pillows.

4. The method of claim 1, wherein the plurality of fluids comprises:
a first phase comprising a solvent and an active agent; and
a second phase comprising a solvent.

5. The method of claim 4, wherein the solvents of the first phase and the second phase are selected from the group consisting of methylene chloride, chloroform, ethyl acetate, benzyl alcohol, diethyl carbonate, methyl ethyl ketone, and water.

6. The method of claim 4, wherein the active agent of the first phase is selected from the group consisting of antioxidants, porosity enhancers, salts, cosmetics, food additives, textile-chemicals, agro-chemicals, plasticizers, stabilizers, pigments, opacifiers, adhesives, pesticides, fragrances, antifoulants, dyes, oils, inks, catalysts, detergents, curing agents, flavors, foods, fuels, herbicides, metals, paints, photographic agents, biocides, propellants, polymer additives, an organic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, colony stimulating factors, growth factors, growth factor analogs, and fragments thereof.

7. The method of claim 4, wherein at least one of the first phase and the second phase comprises a polymer.

8. The method of claim 7, wherein the polymer is selected from the group consisting of poly(d,l-lactic acid), poly(l-lactic acid), poly(glycolic acid), poly(d,l-lactide-co-glycolide) (PLGA), poly(caprolactone), poly(orthoesters), poly(acetals), and poly(hydroxybutryate).

9. A method of preparing an emulsion, the method comprising:
positioning a packing material within a column, the column having a longitudinal axis and a periphery defining an interior cavity, the interior cavity having a longitudinal length; the packing material configured to permit fluid flow through the column along the longitudinal axis, the column comprising:
an inlet in fluid communication with the interior cavity;
an outlet in fluid communication with the interior cavity; and
at least one divider positioned within the interior cavity, each divider of the at least one divider extending along at least a portion of the longitudinal length of the interior cavity,
wherein the at least one divider is configured to partition the packing material and direct fluid flow therethrough the interior cavity;
introducing a plurality of fluids through the inlet of the column under laminar flow conditions, wherein the plurality of fluids comprises: a first phase comprising a solvent and an active agent; and a second phase comprising a solvent, wherein the plurality of fluids combine within the interior cavity of the column to form an emulsion product;
collecting the emulsion product through the outlet of the column; and
wherein the emulsion product comprises a continuous phase that surrounds a dispersed phase containing an active agent;
wherein the method is insensitive to flow rates; and
wherein the column can be utilized at any pressure.

10. A method of preparing an emulsion, the method comprising:
positioning a packing material within a column, the column having a longitudinal axis and a periphery defining an interior cavity, the interior cavity having a longitudinal length; the packing material configured to permit fluid flow through the column along the longitudinal axis, the column comprising:
an inlet in fluid communication with the interior cavity;
an outlet in fluid communication with the interior cavity; and
at least one divider positioned within the interior cavity, each divider of the at least one divider extending along at least a portion of the longitudinal length of the interior cavity,
wherein the at least one divider is configured to partition the packing material and direct fluid flow therethrough the interior cavity;
introducing a plurality of fluids through the inlet of the column under laminar flow conditions, wherein the plurality of fluids comprises: a first phase comprising a solvent and an active agent; and a second phase comprising a solvent, wherein the plurality of fluids combine within the interior cavity of the column to form an emulsion product;
collecting the emulsion product through the outlet of the column;
wherein the emulsion product comprises a continuous phase that surrounds a dispersed phase containing an active agent;
wherein the active agent is dispersed within the dispersed phase;
wherein the method is insensitive to flow rates; and
wherein the column can be utilized at any pressure.

* * * * *